(12) United States Patent
Stenton

(10) Patent No.: US 8,807,859 B2
(45) Date of Patent: Aug. 19, 2014

(54) LIQUID APPLICATOR

(71) Applicant: Advanced Medical Solutions (Plymouth) Limited, Plymouth (GB)

(72) Inventor: Richard J. Stenton, Horrabridge (GB)

(73) Assignee: Advanced Medical Solutions (Plymouth) Limited, Plymouth, Devon (GB)

(*) Notice: Subject to any disclaimer, the term of this patent is extended or adjusted under 35 U.S.C. 154(b) by 0 days.

(21) Appl. No.: 13/733,038

(22) Filed: Jan. 2, 2013

(65) Prior Publication Data

US 2013/0178896 A1    Jul. 11, 2013

Related U.S. Application Data

(63) Continuation of application No. 12/483,209, filed on Jun. 11, 2009, now Pat. No. 8,342,765.

(60) Provisional application No. 61/061,068, filed on Jun. 12, 2008.

(51) Int. Cl.
*B43M 11/06* (2006.01)
*A61B 17/00* (2006.01)

(52) U.S. Cl.
CPC ... *A61B 17/00491* (2013.01); *A61B 2017/0023* (2013.01)
USPC .............. 401/186; 401/183; 222/96; 222/213

(58) Field of Classification Search
USPC ................. 401/183–186, 132–135, 150, 152; 222/95, 96, 207, 212, 213
See application file for complete search history.

(56) References Cited

U.S. PATENT DOCUMENTS 1,313,566 A    8/1919   Trowbridge
2,737,677 A    3/1956   Pasulka
(Continued)

FOREIGN PATENT DOCUMENTS

DE    40 40 620 A1    7/1991
EP    0 858 775        8/1998
(Continued)

OTHER PUBLICATIONS

Burns et al., "Using Tissue Adhesive for Wound Repair: A Practical Guide to Dermabond," American Family Physician, vol. 61, No. 5, Mar. 1, 2000, hand numbered 1-7.

(Continued)

*Primary Examiner* — David Walczak
(74) *Attorney, Agent, or Firm* — Foley & Lardner LLP; Antoinette F. Konski

(57) ABSTRACT

A liquid applicator contains a hollow body portion incorporating a reservoir portion for containing a liquid to be applied by the applicator; an outlet portion having first and second ends, the first end being connected to an outlet mouth of the reservoir; an applicator tip assembly provided on the second end of the outlet portion for discharge of liquid from the reservoir portion via said outlet portion; a plug located in the mouth of the reservoir portion; and actuator for applying an actuating force to the mouth wall to effect movement of the plug towards the outlet portion and for squeezing the walls of the reservoir portion to effect discharge of liquid from the reservoir portion via the outlet portion and the applicator device. The liquid to be dispensed is retained in a reservoir that is sealed by a plug until usage.

17 Claims, 18 Drawing Sheets

(56) References Cited

U.S. PATENT DOCUMENTS

| | | |
|---|---|---|
| 2,761,591 A | 9/1956 | Du Bois |
| 2,784,127 A | 3/1957 | Joyner et al. |
| 3,229,866 A * | 1/1966 | Arbitman et al. ............ 222/453 |
| 3,527,224 A | 9/1970 | Rabinowitz |
| 3,591,676 A | 7/1971 | Hawkins et al. |
| 3,667,472 A | 6/1972 | Halpern |
| 3,995,641 A | 12/1976 | Kronenthal et al. |
| 4,035,334 A | 7/1977 | Davydov et al. |
| 4,183,684 A | 1/1980 | Avery, Jr. |
| 4,444,933 A | 4/1984 | Columbus et al. |
| 4,563,104 A | 1/1986 | Saint-Amand |
| 4,572,689 A | 2/1986 | Chernack |
| 4,650,826 A | 3/1987 | Waniczek et al. |
| 4,784,506 A | 11/1988 | Koreska et al. |
| 4,785,978 A | 11/1988 | Kano et al. |
| 4,925,327 A | 5/1990 | Wirt |
| 4,957,385 A | 9/1990 | Weinstein |
| 5,480,935 A | 1/1996 | Greff et al. |
| 5,538,353 A | 7/1996 | DeHavilland |
| 5,582,596 A | 12/1996 | Fukunaga et al. |
| 5,658,084 A | 8/1997 | Wirt |
| D386,849 S | 11/1997 | Dehavilland |
| 5,752,363 A | 5/1998 | Edwards et al. |
| 5,762,919 A | 6/1998 | Greff et al. |
| 5,772,346 A | 6/1998 | Edwards |
| D396,911 S | 8/1998 | DeHavilland |
| 5,791,801 A | 8/1998 | Miller |
| 5,962,010 A | 10/1999 | Greff et al. |
| 5,975,367 A | 11/1999 | Coelho et al. |
| 5,976,102 A | 11/1999 | Epstein |
| 5,998,472 A | 12/1999 | Berger et al. |
| 6,066,124 A | 5/2000 | Caillouette |
| 6,283,933 B1 | 9/2001 | D'Alessio et al. |
| 6,364,163 B1 | 4/2002 | Mueller |
| 6,475,502 B1 | 11/2002 | Lee et al. |
| 6,477,743 B1 | 11/2002 | Gross et al. |
| 6,536,975 B1 * | 3/2003 | Tufts ............................ 401/134 |
| 6,547,467 B2 | 4/2003 | Quintero |
| 6,592,281 B2 | 7/2003 | Clark et al. |
| 6,595,940 B1 | 7/2003 | D'Alessio et al. |
| 6,673,031 B2 | 1/2004 | Mark |
| 6,705,790 B2 | 3/2004 | Quintero et al. |
| 6,729,786 B1 | 5/2004 | Tufts et al. |
| 6,766,817 B2 | 7/2004 | da Silva |
| 6,918,404 B2 | 7/2005 | Dias da Silva |
| 6,991,393 B2 | 1/2006 | Tufts et al. |
| 6,991,394 B2 | 1/2006 | Tufts et al. |
| 7,044,937 B1 | 5/2006 | Kirwan et al. |
| 7,066,586 B2 | 6/2006 | da Silva |
| 7,094,250 B2 | 8/2006 | Stenton |
| 7,182,536 B2 | 2/2007 | Tufts et al. |
| 7,182,539 B2 * | 2/2007 | Pan et al. ...................... 401/186 |
| 7,306,390 B2 | 12/2007 | Quintero et al. |
| 7,516,872 B2 | 4/2009 | Boone et al. |
| 8,323,260 B2 | 12/2012 | Stenton |
| 2003/0015557 A1 | 1/2003 | D'Alessio et al. |
| 2003/0032980 A1 | 2/2003 | Stenton |
| 2003/0060746 A1 | 3/2003 | Mark |
| 2003/0080151 A1 | 5/2003 | D'Alessio et al. |
| 2003/0236573 A1 | 12/2003 | Evans et al. |
| 2004/0074925 A1 | 4/2004 | Faurie |
| 2004/0079766 A1 | 4/2004 | Kokubo |
| 2004/0254561 A1 | 12/2004 | Stenton |
| 2005/0025559 A1 | 2/2005 | Stenton |
| 2005/0042196 A1 | 2/2005 | Askill et al. |
| 2005/0047845 A1 | 3/2005 | White et al. |
| 2006/0049203 A1 | 3/2006 | Boone et al. |
| 2006/0072959 A1 | 4/2006 | Tufts et al. |
| 2006/0180613 A1 | 8/2006 | Manesis |
| 2008/0046004 A1 | 2/2008 | Stenton |
| 2008/0167681 A1 | 7/2008 | Stenton |

FOREIGN PATENT DOCUMENTS

| | | |
|---|---|---|
| EP | 1 445 032 A2 | 8/2004 |
| EP | 1 337 455 | 1/2007 |
| JP | 01-025843 | 1/1989 |
| WO | WO-95/31138 | 11/1995 |
| WO | WO-96/40797 | 12/1996 |
| WO | WO-02/46089 | 6/2002 |
| WO | WO-02/47602 A2 | 6/2002 |
| WO | WO-2004/110282 | 12/2004 |
| WO | WO-2008/001067 A2 | 1/2008 |

OTHER PUBLICATIONS

Second Collegiate Edition, American Heritage Dictionary, 1976, p. 121.

Notice of Allowance dated Nov. 17, 2010 in U.S. Appl. No. 10/460,646.

Patent Board Decision dated Aug. 16, 2010 in U.S. Appl. No. 10/460,646.

Examiner's Answer to Appeal Brief dated Apr. 13, 2009 in U.S. Appl. No. 10/460,646.

Advisory Action dated Aug. 1, 2008 in U.S. Appl. No. 10/460,646.

Final Office Action dated Feb. 7, 2008 in U.S. Appl. No. 10/460,646.

Non-Final Office Action dated Aug. 22, 2007 in U.S. Appl. No. 10/460,646.

Final Office Action dated Mar. 21, 2007 in U.S. Appl. No. 10/460,646.

Non-Final Office Action dated Jul. 3, 2006 in U.S. Appl. No. 10/460,646.

Notice of Allowance dated Aug. 2, 2012 in U.S. Appl. No. 13/028,987.

Ex Parte Quayle Action dated May 11, 2012 in U.S. Appl. No. 13/028,987.

* cited by examiner

LIQUID APPLICATOR

CROSS-REFERENCE TO RELATED APPLICATION

This application is a continuation application of U.S. application Ser. No. 12/483,209, filed Jun. 11, 2009, now U.S. Pat. No. 8,342,765, issued Jan. 1, 2013, which claims benefit under 35 U.S.C. §119(e) of U.S. Provisional Application No. 61/061,068, filed Jun. 12, 2008, which are incorporated herein by reference in their entirety.

FIELD OF THE INVENTION

The present invention relates to applicators for liquids, e.g. adhesives, sealants and coatings. The invention relates particularly (but not necessarily exclusively) to liquid applicators for use in applying medical adhesives, sealants and coatings to skin wounds. Applicators of the invention are intended particularly (but again not necessarily exclusively) to be of the single-use, disposable type. The term liquid as used herein is intended to encompass gels and pastes.

BACKGROUND

Applicators for small to medium quantities of liquid medical adhesives, sealants and coatings (particularly those that polymerise on application, e.g. cyanoacrylates) tend to be based on mechanical rupture of a thin-walled glass or plastic ampoule contained within a flexible walled plastics housing. The squeezing of the applicator housing causes rupture of the ampoule thus allowing the liquid to be discharged through an outlet of the applicator.

Typical of the state of the art is the Duraprep™ applicator made by 3M whereby a lever is depressed causing deformation and breakage of an internal ampoule thereby releasing the enclosed fluid. Similarly the DERMABOND™ applicator made by James Alexander consists of a flexible tube which is compressed between thumb and forefinger to crush a thin-walled glass ampoule and release the fluid for dispensing. The applicators incorporate a porous component which is intended to allow discharge of the liquid but retain pieces of fractured glass within the applicator. However these applicators nevertheless can expose the user or patient to the risk of contact with broken glass.

It is therefore an object of the present invention to obviate or mitigate the above mentioned disadvantages.

SUMMARY OF THE INVENTION

According to the present invention there is provided a liquid applicator comprising:

(a) a hollow body portion incorporating (i) a reservoir portion for containing a liquid to be applied by the applicator, and (ii) an outlet portion having first and second ends, the first end being connected to an outlet mouth of the reservoir, (b) an applicator tip assembly provided on the second end of the outlet portion for discharge of liquid from the reservoir portion via said outlet portion, (c) a plug located in the mouth of the reservoir portion, said plug and mouth being configured so that the plug is moveable towards the applicator tip assembly from a first position at which it seals the reservoir portion to a second position at which fluid may follow out of the reservoir portion, and (d) actuator means for applying an actuating force to the mouth wall to effect movement of the plug towards the outlet portion and for squeezing the walls of the reservoir portion to effect discharge of liquid from the reservoir portion via the outlet portion and the applicator device.

BRIEF DESCRIPTION OF THE DRAWINGS

The invention will be further described by way of example only with reference to the accompanying drawings, in which:

FIGS. 13a and 13b show (to an enlarged scale) respectively a side view of the plug of the applicator assembly and an end view of the plug as seen in the direction of arrow X in FIG. 13a;

DETAILED DESCRIPTION OF THE INVENTION

Figure 1:
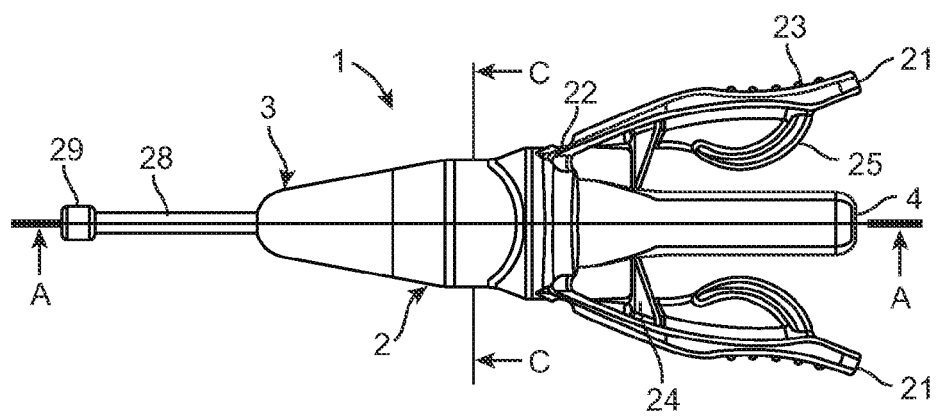
FIG. 1 is a plan view of a first embodiment of liquid applicator in accordance with the invention.
Figure 2:
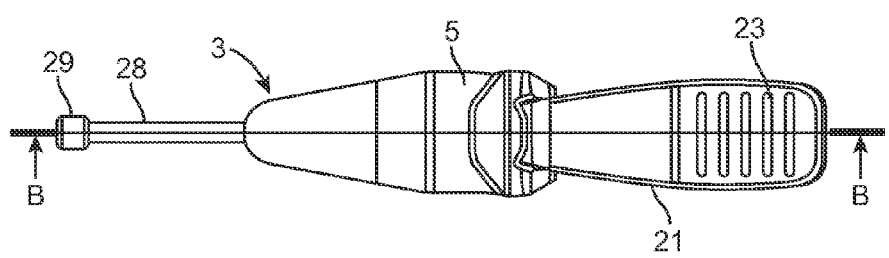
FIG. 2 is a side view of the liquid applicator shown in FIG. 1.

Before the present compositions, and methods are described, it is to be understood that the invention is not limited to the particular methodologies, protocols, and devices described, as these may vary. It is also to be understood that the terminology used herein is intended to describe particular embodiments of the present invention, and is in no way intended to limit the scope of the present invention as set forth in the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All technical and patent publications cited herein are incorporated herein by reference in their entirety. Nothing herein is to be construed as an admission that the invention is not entitled to antedate such disclosure by virtue of prior invention.

In accordance with the present invention and as used herein, the following terms are defined with the following meanings, unless explicitly stated otherwise.

As used in the specification and claims, the singular form "a", "an" and "the" include plural references unless the context clearly dictates otherwise.

All numerical designations, e.g., pH, temperature, time, concentration, and molecular weight, including ranges, are approximations which are varied (+) or (−) by increments of 0.1 or 1.0, where appropriate. It is to be understood, although not always explicitly stated that all numerical designations are preceded by the term "about". It also is to be understood, although not always explicitly stated, that the reagents described herein are merely exemplary and that equivalents of such are known in the art.

As used herein, the term "alkyl" refers to monovalent saturated aliphatic hydrocarbyl groups having from 1 to 10 carbon atoms and, in some embodiments, from 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

As used herein, the term "alkenyl" refers to a linear or branched hydrocarbyl group having from 2 to 10 carbon atoms and in some embodiments from 2 to 6 carbon atoms or 2 to 4 carbon atoms, and having at least 1 site of vinyl unsaturation (>C=C<). For example, ethenyl, propenyl, 1,3-butadienyl, and the like.

As used herein, the term "alkoxy" refers to the group —O-alkyl wherein alkyl is as defined herein. Alkoxy includes, by way of example, methoxy, ethoxy, n-propoxy, isopropoxy, n-butoxy, t-butoxy, and sec-butoxy.

As used herein, the term "alkynyl" refers to a linear monovalent hydrocarbon group or a branched monovalent hydrocarbon group containing at least one triple bond. The tel "alkynyl" is also meant to include those hydrocarbyl alkyl groups having one triple bond and one double bond. For example, ethynyl, propynyl, and the like.

As used herein, the term "aryl" or "ar" in "aralkyl" refers to an aromatic group of from 6 to 14 carbon atoms and no ring heteroatoms and having a single ring (e.g., phenyl) or multiple condensed (fused) rings (e.g., naphthyl or anthryl).

As used herein, the term "aralkyl" refers to an alkyl substituted with an aryl, where alkyl and aryl are as defined herein. Thus, "arylalkyl" refers to groups such as, for example, benzyl, methylbenzyl, phenylethyl, and the like.

As used herein, the term "comprising" or "comprises" is intended to mean that the devices and methods include the recited elements, but not excluding others. "Consisting essentially of" when used to define devices or methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace amount of elements of other ingredients and substantial method steps. Embodiments defined by each of these transition terms are within the scope of this invention.

As used herein, the term "cycloalkyl" refers to a saturated or partially saturated cyclic groups of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom. Examples of cycloalkyl groups include, for instance, cyclopropyl, cyclobutyl, cyclopentyl, cyclooctyl, and cyclohexenyl.

In the applicator of the invention, therefore, the liquid to be dispensed is retained in a reservoir that is sealed by a plug until usage. The first actuator formations on the applicator are capable of dislodging the plug so as to create a path to allow liquid to flow out of the reservoir portion. Subsequently the second actuator formations are employed to squeeze the walls of the reservoir portion and effect discharge of the liquid. Thus the applicator of the invention avoids the use of a glass ampoule and the attendant possible dangers associated with fractured glass.

The applicator of the invention is particularly suitable for use in conjunction with liquid adhesives, sealants and coatings particularly for medical applications. The applicator is particularly suitable for use with liquid cyanoacrylate compounds that polymerise on exposure to air.

The hollow body portion is such that at least the walls of the reservoir portion are of flexible material to allow the actuator means to squeeze the walls of the reservoir portion to effect controlled discharge of liquid therefrom. Preferably the hollow body portion is wholly of a flexible material e.g. polyethylene or polypropylene, both of which have good flexibility and moisture barrier properties. The polyethylene and polypropylene may be of either high or low density The plug is ideally of a different material to that of the body to reduce the possibility of the plug and body sticking together. The plug may for example be of polyethylene or polypropylene (both of either high or low density), although ideally a different material from that of the body portion. Alternatively the plug may be of an acetal.

It is also envisaged that the body portion and/or the plug may have a low friction surface (at least in their regions which provide the seal) to reduce the potential of sticking and malfunction. The low friction surface may be provided by an additive at the surface such as PTFE in powder or fibre form. Alternatively the surface of the body portion and/or plug may be manufactured of a fluorinated polymer. Thus, for example, the plug or body portion may have a fluorinated surface, such as provided by PTFE. By way of example, the plug may be of an acetal impregnated with PTFE in either a powder or fibre form. Alternatively the plug may be manufactured from PTFE or FEP or other flouro plastics. The provision of fluorinated material at the surface of the body portion and/or plug (at least in their regions which provide the seal) not only reduces the potential of sticking and malfunction but also improves resistance to moisture ingress.

In a preferred embodiment of the invention, the plug has a head that is a sliding fit on the inner surface of the outlet portion and a shank with a first portion that sealingly locates within the mouth of the reservoir portion. The first portion of the plug shank may be provided with "sealing rings" which whilst providing good sealing capability also reduce resistance to movement during the actuation process. Additionally the inner surface of the outlet portion (on which the head of the plug is slideable) is formed with at least one flow channel which extends from the first end of the outlet portion towards the second end. Preferably a plurality of such flow channels are provided (most preferably equally spaced around the inner surface of the outlet portion) and extend parallel to each other, each such channel preferably being linear.

In use of the applicator, operation of the actuator means initially causes the plug to move to the second position. As a result of this movement, the head of the plug moves forward and disengages with the body. With subsequent squeezing of the walls of the reservoir by the actuator means, the liquid may pass out of the reservoir portion and then past the head of the plug via the flow channel(s) formed in the inner surface of the outlet portion. Consequently by virtue of the flow channel(s) the liquid can travel from the reservoir portion to the applicator tip assembly for discharge from the applicator device.

In a preferred embodiment of the invention, the actuator means comprises a first actuator formation for causing the plug to move to the second position and a second actuator formation for subsequent squeezing of the walls of the reservoir.

In certain embodiments of the invention, the end of the head of the plug nearest the applicator tip assembly may, if the plug travels sufficiently far, abut against an internal surface of the applicator device. For such cases, the said end of the head is configured to divert flow of liquid from along the flow channels inwardly towards the centre of the outlet portion for subsequent discharge via the applicator tip assembly. This configuration may be provided for by castellations or similar channels extending around the periphery of the end of the head. Thus once the head has abutted against the aforementioned internal surface the castellations effectively define ports through which liquid may pass towards the interior of the outlet portion.

Preferably also the first portion of the shank has over a length thereof a cross-section (preferably circular) which sealingly locates in a corresponding cross-section over a length of the mouth of the reservoir portion. Movement of the plug to its second position causes said first portion of the shank to move out of the mouth of the reservoir portion.

For preference, there is a step between said head and said first portion of the shank. In this case the inner surface of the outlet portion of the body is provided with a shoulder that faces away from the reservoir portion and the step of the plug abuts against said shoulder when the plug is in its first position.

It is also preferred that, at its end opposite the head, the shank has a second portion which is of lesser cross-section than said first portion. This second portion may remain located within the mouth of the reservoir when the plug has been moved to its second position so that the liquid is able to flow through a gap defined between the wall of the mouth and this second portion.

For all embodiments of the invention, it is preferred that the mouth of the reservoir portion is formed with walls that converge towards each other in a direction going away from the applicator tip assembly. A portion of the plug (ideally the above mentioned second portion of the shank) locates between these converging walls. Additionally the preferred actuator is provided with at least one (and more preferably two, although more than two may be provided) actuator means which when operated provide an actuating force to the converging walls, the actuating force having a component directed towards the tip assembly. This actuating force effects movement of the plug towards the second end of the outlet formation. The actuator means may be configured to be operated by the fingers and/or thumb of a user of the device and may be such as to provide a mechanical advantage whereby the force applied to the actuator means by the finger(s) and/or thumb of the user results in a higher actuating force applied to the converging wall of the applicator.

Most conveniently, the applicator has a pair of opposed actuator means in the form of wings or levers (herein referred to simply as levers for convenience) each of which is provided with a first actuator formation and a second actuator formation. The levers are preferably biased away from each other and are pivotally mounted on the body of the applicator for movement towards and away from each other. Squeezing of the levers together initially causes the first actuator formations to dislodge the plug. Further squeezing of the levers causes the second actuator formations to engage the walls of the reservoir portion to effect discharge of the liquid.

The first actuator formations may be in the form of prongs whereas the second actuator formations preferably have arcuate surfaces for squeezing the walls of the reservoir portion. Alternatively the first and second actuator formations of any one lever may comprise a continuously curved component with the second actuator formation being of shallower curvature than the first actuator formation.

FIGS. 1-9 of the drawings relate to a first embodiment of liquid applicator 1 that can be used to apply diverse types of fluids. It is particularly well-suited for use with sterilisable fluids for therapeutic applications to ma alian tissue, including topical liquids such as tissue adhesives for surgical applications, coatings and sealants. The liquid may for example be a cyanoacrylate prepolymer and the applicator will be described with specific reference to such a compound (although as indicated it is suitable for other liquids).

In broad outline, the applicator 1 is for use in applying a fine line of liquid, polymerisable cyanoacrylate adhesive to a skin wound so as to effect closure and/or sealing thereof. The applicator 1 comprises a hollow body 2 on which is mounted an applicator tip assembly 3 (see particularly FIGS. 3 and 4). The cyanoacrylate adhesive (indicated by cross-hatched lines in FIG. 3) is held in a flexible-walled reservoir portion 4 of the applicator body 2 and is discharged when required via the applicator tip assembly 3 which is configured to apply the adhesive as the aforementioned fine line. The cyanoacrylate adhesive is retained in the reservoir portion 4 until required by means of a moveable plug 12 (see FIGS. 3 and 4) and discharge is effected by squeezing together (between the forefinger and thumb of one hand) two levers 21 which are adapted initially to dislodge the plug 12 (to allow liquid flow out of the reservoir portion 4) and then press on walls of the reservoir portion 4 to discharge the cyanoacrylate adhesive through the applicator tip assembly 3.

Figure 8:
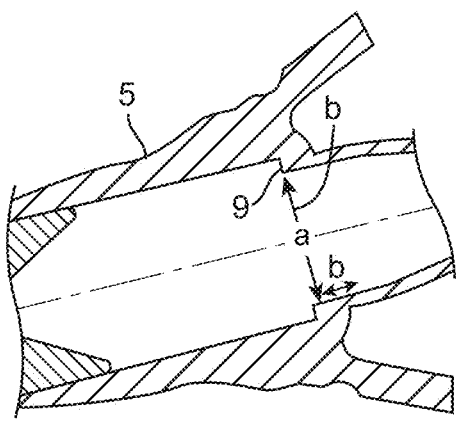
FIG. 8 is similar to FIG. 7 but omitting details of the plug.

Body portion 2 is moulded from High Density Polyethylene (HDPE) and is formed with the aforementioned reservoir portion 4 which is connected to an outlet portion 5 of the body 2 at a mouth 6 of the reservoir portion 4 (see FIG. 8). At its end opposite the reservoir portion 4, the outlet portion 5 serves to locate the applicator tip assembly 3 in position.

Figure 3:
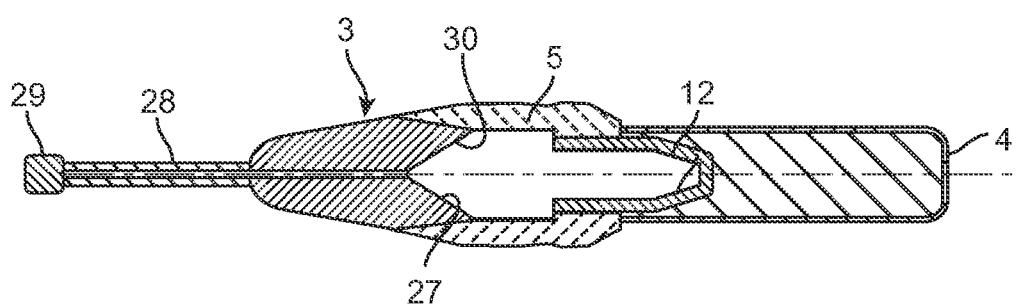
FIG. 3 is a sectional view of the liquid applicator taken along the line A-A in FIG. 1.
Figure 4:
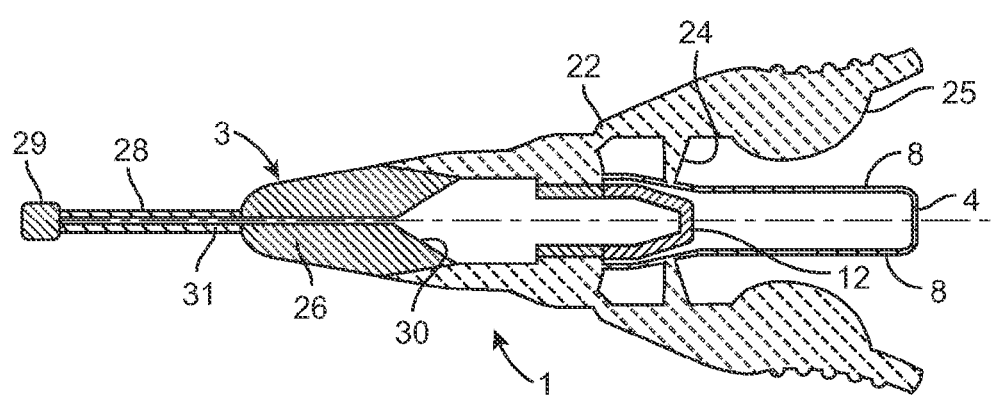
FIG. 4 is a sectional view of the liquid applicator taken along the line B-B in FIG. 2.
Figure 5:
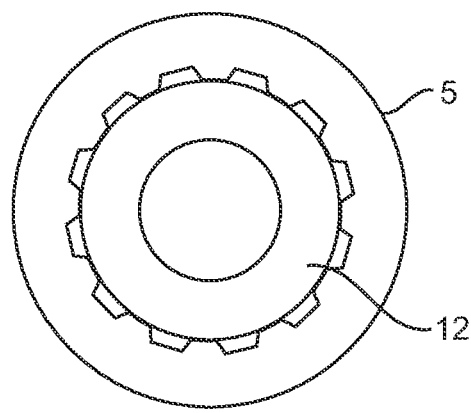
FIG. 5 is a sectional view to an enlarged scale of the liquid applicator taken along the line C-C in FIG. 1.
Figure 6:
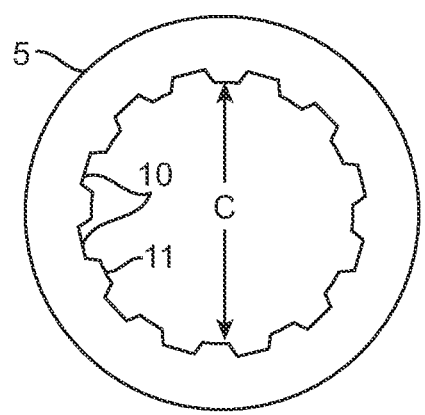
FIG. 6 is similar to FIG. 5 but omits details of the plug.
Figure 7:
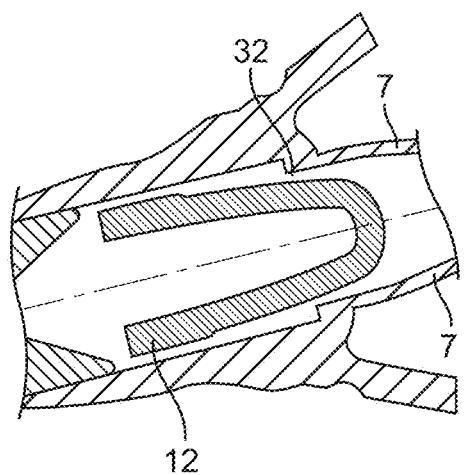
FIG. 7 is a detail to an enlarged scale of a portion of the applicator as illustrated in FIG. 4 but showing the plug positioned off its seat.

FIGS. 4 and 6 show that the mouth 6 is defined partly by two opposed walls 7 that converge towards each other in a direction going away from the applicator tip assembly 3 (i.e. the walls converge towards the right hand end of the liquid applicator 1 as viewed in FIGS. 3 and 4). At the limit at their convergence, the walls 7 are extended as walls 8 that define two opposed sides of the reservoir portion 4. Since the body portion 2 (and thus the reservoir portion 4) is of moulded HDPE, the walls 7 and 8 have a degree of flexibility which is provided for the purposes described more fully below.

Referring now to FIG. 8, it will be seen that the inner wall of the outlet portion 5 is formed at its end adjacent the mouth 6 with an annular shoulder 9 which faces towards the applicator tip assembly 3. At the shoulder 9, the mouth 6 is referenced as having a diameter a which is constant over a distance b going towards the interior of the reservoir portion 4.

A plurality of circumferentially spaced, axially extending grooves 10 which are of generally trapezoidal cross-section (see FIGS. 5 and 6) are formed in the interior wall of the outlet portion 5 and extend from the shoulder 9 to the applicator tip assembly 3. Expressed alternatively, the inner surface of the outlet portion 5 can in cross-section be seen to comprise alternating trapezoidal section grooves 10 and trapezoidal section ribs 11 (see FIGS. 5 and 6). The distance between the crests of 2 diametrically opposed ribs 11 is referenced in FIG. 6 as c. Furthermore the distance that the shoulder 9 projects radially inwardly of the crest of a rib 11 is shown.

Figure 9:
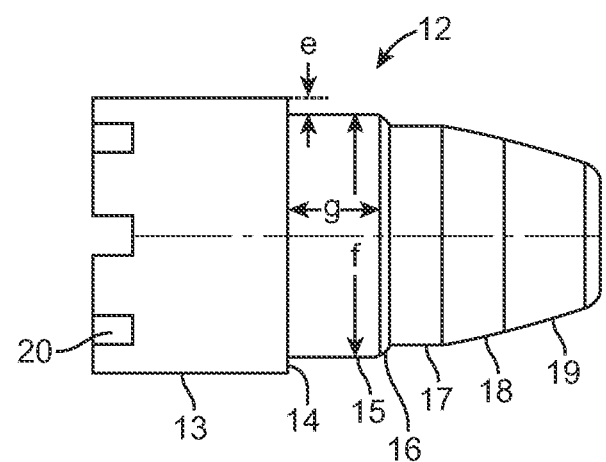
FIG. 9 is a detail to an enlarged scale of the plug of the applicator.
Figure 10:
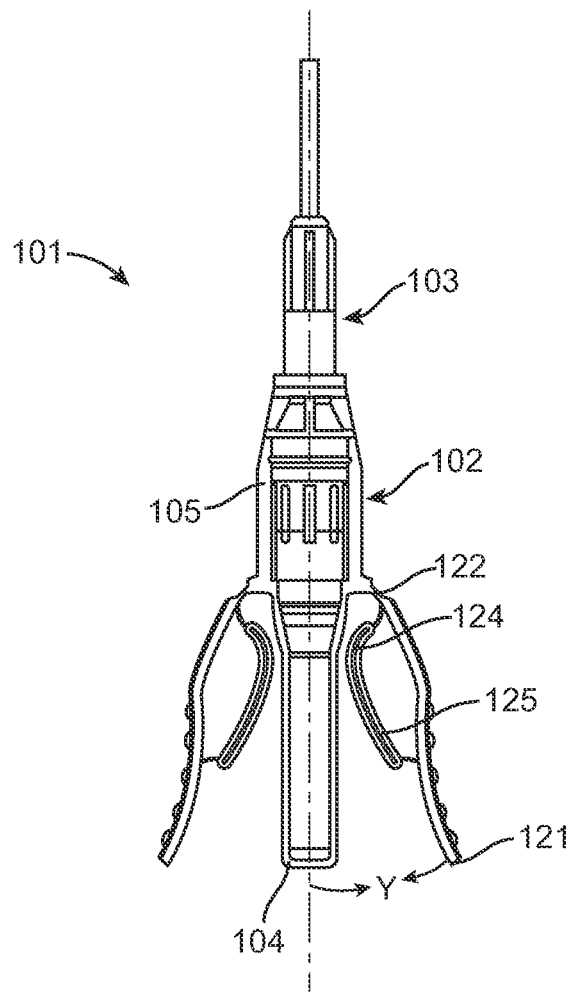
FIG. 10 is a plan view of a second embodiment of liquid applicator in accordance with the invention.

FIGS. 3 and 4 show the aforementioned plug 12 that serves to retain liquid cyanoacrylate in the reservoir portion 4 and prevent it passing to the outlet portion 5 (and thus to the applicator tip assembly 3) until the plug 12 is dislodged, as described more fully below. Specific detail of the plug 12 is shown in FIG. 9 to which reference is now made. Plug 12 is of moulded polypropylene and (at the left hand end as viewed in FIG. 9) has a cylindrical head region 13 having an external diameter (the maximum cross-section for the plug 12) which is the same as c (i.e. the distance between the crests of 2 diametrically opposed ribs 11) so as to make the head 13 a close sliding fit on the interior of the outlet portion 5. Going towards the opposite end of the plug 12, there is a shank with the following successive formations, namely:

(i) a radially inwardly directed, right-angled step 14 having a depth e which is the same as to the distance by which the shoulder 9 projects beyond the crests of the ribs 11;
(ii) a cylindrical, first intermediate region 15 having an external diameter f which is the same as the diameter a of the mouth 6 of the reservoir portion 4 and a length g which is the same as b;
(iii) a frustoconical step 16 converging away from the cylindrical region 15;
(iv) a cylindrical, second intermediate region 17;
(v) a tapering third intermediate portion 18; and
(vi) an end portion 19 that tapers at a slightly sharper angle than intermediate portion 18.

A further feature of the plug 12 in the provision of castellations 20 around the free end of head 13. The function of these castellations 20 is described below.

Purely for the purposes of moulding, plug 12 is hollow (to ensure the required tolerances) and is open at the head 13 and closed at the opposite end of tapering portion 19.

Integrally moulded with the exterior of the outlet portion 5 of the body and spaced 180° apart from each other, are the two levers 21. More particularly, each lever 21 is integrally connected to the body portion 5 by a flexible neck 22 such that the levers 21 may be squeezed together but when released resile to their original position. For the purposes of being squeezed together, each lever 21 is provided with a respective finger/thumb grip formation 23, the arrangement being such that the finger/thumb grip formations 23 may be held between the thumb and forefinger of one hand. Each lever has a prong formation 24 which with the levers 21 being in their original position (i.e. without the levers being squeezed together) just comes into contact with a respective wall 7 of the mouth 6 of reservoir portion 4. Each prong formation 24 is angled slightly away from the free end of the respective lever 21 for reasons which will be described more fully below. Each lever 21 additionally formed with two generally arcuate actuator formations 25 which, on squeezing levers 21 together beyond a certain point, come into contact with the walls 8 of reservoir portion 4.

The liquid applicator 1 is completed by the applicator tip assembly 3 which has the structure illustrated in FIGS. 3 and 4. More particularly, applicator tip assembly 3 has a body 26 formed at one end as a spigot 27 for locating assembly 3 as a push-fit on the free end of outlet portion 5 (the spigot 27 being located in engagement with the interior surface of outlet portion 5) and being provided at the other end with an elongate probe 28 itself provided with a fibrous applicator tip 29 at its free end. Although not shown in FIGS. 3 and 4, the spigot 27 may have a circumferential ridge for location in a complementary annular groove (again not shown) extending around the inner surface of outlet portion 5. Such a ridge and groove arrangement serves not only to locate the body portion 2 and applicator tip assembly 3 together but also provides for leak free operation of the liquid applicator 1. The end of the spigot 27 converges towards the probe 28 as shown so as to provide a "funnel" 30 which leads into a narrow bore 31 extending along the length of the remainder of the body 26 and throughout the length of the probe 28.

Assembly and use of the liquid applicator 1 will now be described.

Body portion 2 (with an integral levers 21), applicator tip assembly 3 and plug 12 are initially provided as three separate, moulded components.

Prior to assembly of the device, the body portion 2 is positioned vertically (outlet portion 5 uppermost) and the reservoir portion 4 is filled to the required level with liquid cyanoacrylate adhesive to be dispensed by the device.

In the next step of assembly, the tapering end 19 of plug 12 is inserted into the open end of outlet portion 5 and the plug 12 is pushed along the latter portion until its step 14 comes into abutting engagement with the shoulder 9. During this movement, the cylindrical region 15 of the plug 12 enters the mouth 6 and forms a seal over the aforementioned distance b so that the liquid cyanoacrylate adhesive is prevented from being discharged.

Applicator tip assembly 3 may now be located as a push-fit on the free end of outlet portion 5 so as to produce the device as illustrated in FIGS. 1-4.

In order to discharge liquid cyanoacrylate adhesive from the applicator 1, the two levers 21 may be gripped between the thumb and forefinger of one hand and squeezed together. Initially this squeezing together of the levers causes the prongs 24 to act against the walls 7 and apply a force which causes the plug 12 to move to the position illustrated in FIG. 7 (i.e. the plug moves to the left from its position shown in FIGS. 3 and 4) such that its cylindrical region 15 is moved wholly clear of the mouth 6 of the reservoir portion 4. There is now an annular gap 32 between the shoulder 9 (of the outlet portion 5) and the plug 12 which is allowed for by the configuration of its frustoconical step 16 and tapering region 18 and 19. Consequently the interior of the reservoir portion 4 is now in communication (via the annular gap 32) with the trapezoidal cross-section channels 10 formed in the inner wall of the outlet portion 5.

Continued squeezing of the levers 21 together causes the arcuate actuators 25 to engage and squeeze the walls 8 of the reservoir portion and cause liquid contained therein to be expressed through the annular gap 32 and along the channels 10. Liquid is therefore able to flow along the channels 10 and into the funnel-section 30 at the spigot end of the applicator tip assembly and then along the narrow bore for discharge via the fibrous tip 29. As the levers 21 are squeezed, the adhesive exits the tip 29 and results in a vacuum being created behind the adhesive left in the reservoir portion 4. Once the wings 21 are released, this vacuum draws adhesive back from the tip 29 thereby preventing drips and improving application control. Release of the levers 21 (so that arcuate actuators 25 no longer contact the walls 8) allow the walls 8 to return to their original position and cause a suction force to be generated which causes liquid to be drawn backwardly into the device.

Thus the device is capable of accurately applying only small amounts of liquid and of terminating the application when desired.

Reference is now made to FIGS. 10-15 of the drawings which relate to a second embodiment of liquid applicator 101. It will be seen from these figures that the second embodiment of liquid applicator 101 has marked similarity with the first embodiment of liquid applicator 1 described with reference to FIGS. 1-9. Therefore for the sake of convenience those parts of the applicator 101 which correspond with an equivalent part in the liquid applicator 1 are referenced by a numeral which is one hundred greater than the corresponding reference numeral in FIGS. 1-9. Thus purely by way of example the body portion of the applicator 101 is denoted by the reference numeral 102 (cf reference numeral 2 used for the body portion of liquid applicator 1).

In view of the similarities between the first embodiment of liquid applicator 1 and second embodiment of liquid applicator 101 only a brief description of the latter will be given so as to highlight certain features.

One particular feature of difference between the first embodiment of liquid applicator 1 and the second embodiment of liquid applicator 101 lies in the first and second actuator formations. In the liquid applicator 1 the first actuator formation 24 is depicted as being a prong and the second actuator formation 25 being arcuate. In contrast, the first and second actuator formations 124 and 125 in the second embodiment of liquid applicator 101 are each formed as part of a continuously curving component with the first actuator formation 124 being of more pronounced curvature than the second actuator formation 125.

The manner in which the first and second actuator formations 124 and 125 function to effect discharge of the contents of the applicator 101 is described below with reference to FIGS. 14a-e.

Figure 11:
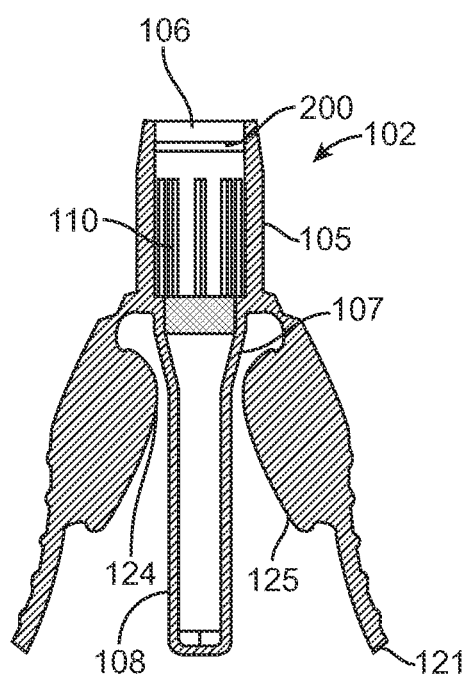
FIG. 11 is a cross-sectional view of the hollow body of the liquid applicator illustrated in FIG. 10.

Further detail of the body portion 102 (with its integral levers 121) is seen in the cross-section of FIG. 11 which clearly shows (some of) the longitudinal grooves or flow channels 110 that are formed in, and extend in parallel along, the inner wall of the outlet portion 105. Additionally shown in FIG. 11 is a circumferential (i.e. annular) groove 200 formed on the inner surface of the outlet portion 105 in a region thereof between its open end and the ends of the grooves 110.

Figure 12:
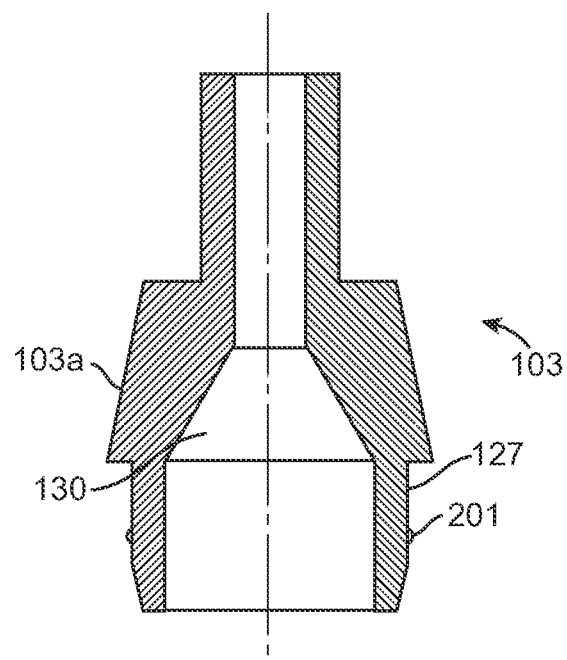
FIG. 12 is a cross-sectional view of part of the applicator tip assembly (but omitting the actual tip) of the applicator illustrated in FIG. 10.

A cross-section of part of the applicator assembly 103 is shown in FIG. 12. In fact, in the embodiment of FIGS. 10-15, the applicator assembly may be in two parts, one of which is shown in FIG. 12 referenced as 103a and the other part of which (not shown in FIG. 12) is the applicator tip. With such an arrangement, it will be appreciated that different applicator tips may be mounted on part 103a depending on the intended use of the device. With further reference to FIG. 12 it will be seen that part 103a includes a circumferential ridge 201 on the spigot 127. It will be appreciated that the circumferential groove 200 on the body portion 102 and the circumferential ridge 201 co-operate during assembly of the applicator 101 so as to locate the body portion 102 and applicator tip assembly 103 together and to provide for a leak free operation.

Figure 13A:
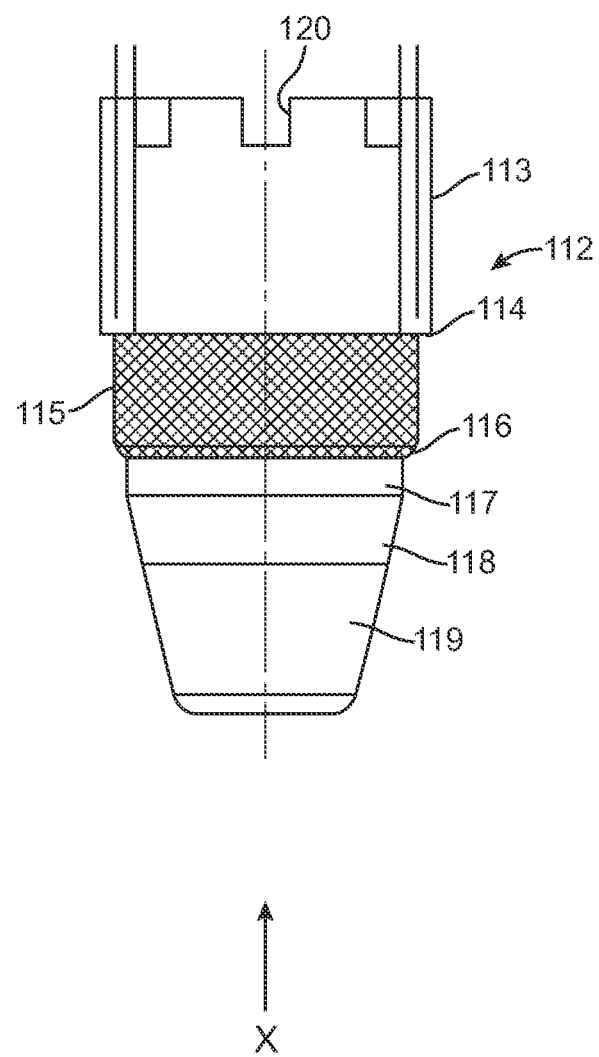
Figure 13B:
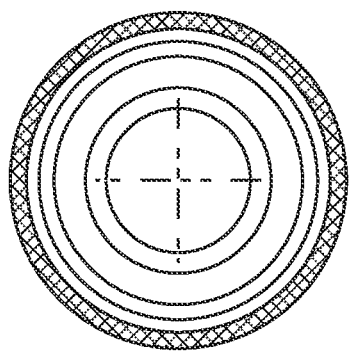

Side and end views of the plug 112 are shown in FIGS. 13a and 13b respectively. The cylindrical first intermediate region 115 and frustoconical step 116 are shown in FIG. 13a with cross-hatched shading. This is to represent the sealing area of the plug which is intended to cooperate with the correspondingly cross-hatched area within the body portion 102 as shown in FIG. 11. In the regions of these cross-hatched areas the plug and/or body portion may be specially treated to ensure a leak free seal between the plug and the body to reduce coefficient of friction. In a modified construction (not shown in the drawings) the region 115 of the plug 112 may be provided with sealing rings to prevent egress of liquid (from reservoir 104 until the plug 112 has been dislodged from its seated position.

Reference is now made to FIGS. 14a-14e which are "see-through" views of the liquid applicator 101 illustrating the location of the plug 112 for various angular positions of the levers 121.

Figure 14C:
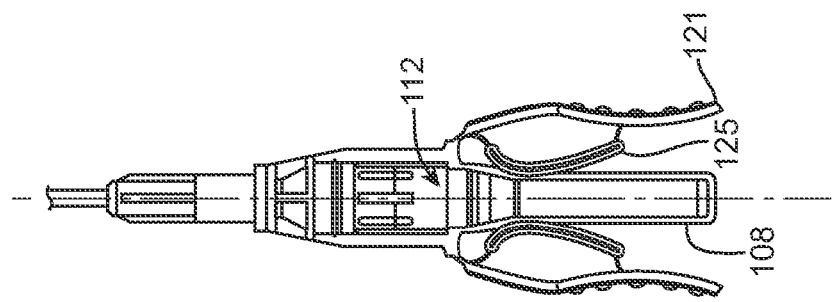
FIGS. 14a-e are views (to an enlarged scale) of a portion of the actuator assembly illustrated in FIG. 10 with the actuating levers at various positions.
Figure 14B:
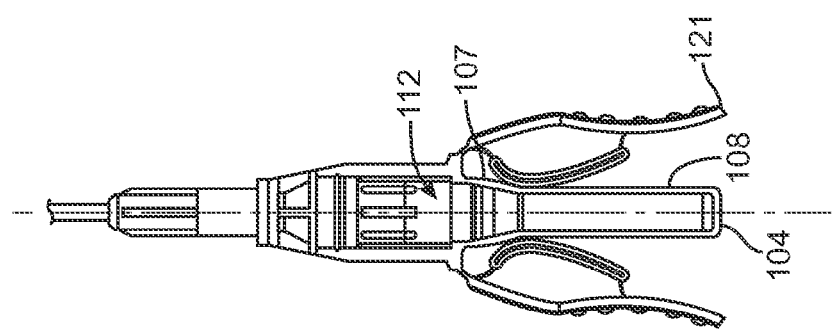
Figure 14A:
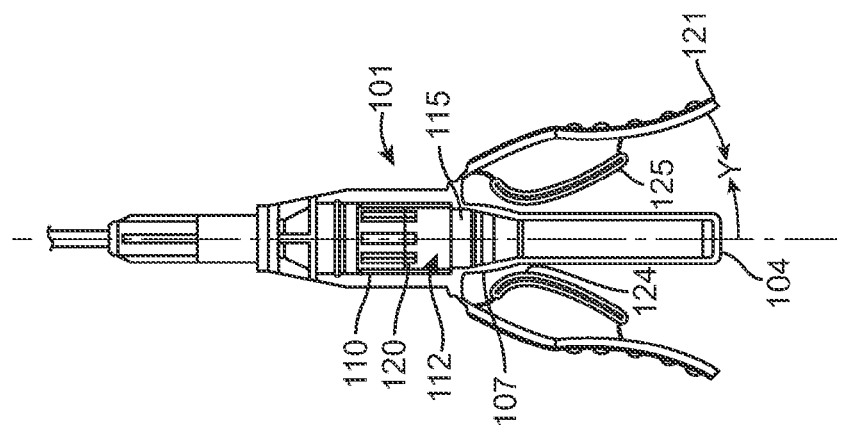

In more detail, FIG. 14a shows the situation where the levers 121 are relaxed so that the actuator formations 124 and 125 are out of contact with the reservoir portion 104. Squeezing of the levers 121 together so that they are deflected by 7 degrees from the position illustrated in FIG. 14a brings them to the position shown in FIG. 14b in which the first actuator formation 124 has just come into contact with the reservoir portion 104 (more particularly the walls 107 thereof).

Movement of the levers 121 by a further 3 degrees (i.e. 10 degrees from the position shown in FIG. 14a) brings them to the position shown in FIG. 14c in which the first actuator formations 124 have caused the plug 112 to be dislodged slightly (i.e. moved upwardly as viewed in the drawing) as compared to the position in FIGS. 14a and 14b and the second actuator formations 125 are beginning to act against the walls 108 of the reservoir 104. However at this position the cylindrical, first intermediate region 105 of the plug 112 still locates within the mouth 106 of the reservoir portion 104 so that adhesive is retained within the reservoir portion 104.

Figure 14D:
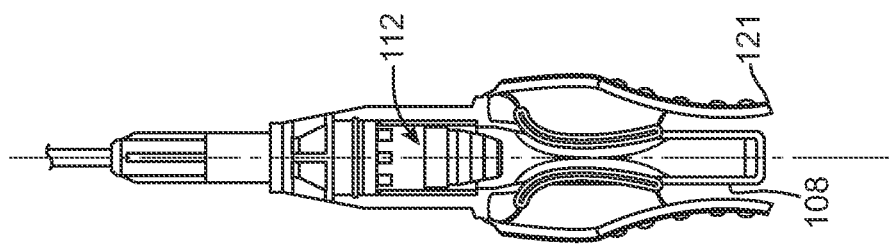

Once the levers 121 have been deflected by 16 degrees from their original position shown in FIG. 14a, the condition shown in FIG. 14d is reached. At this point the cylindrical, first intermediate region 115 of the plug 112 has moved by a distance g so that it (the first intermediate portion 115) has just moved out of the mouth 106. In fact, if the applicator 101 were turned "upside-down" from the upright position illustrated in FIG. 14d then the plug 112 would move vertically down under gravity. It will be noted from FIG. 14d that the second actuator formations 125 are now applying significant compressive force to the walls 108 reservoir 104.

Figure 14E:
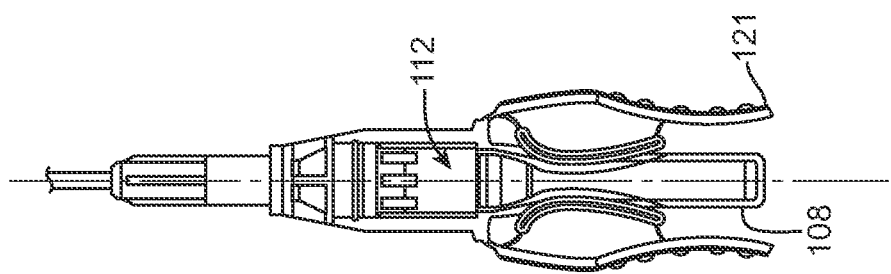
Figure 15:
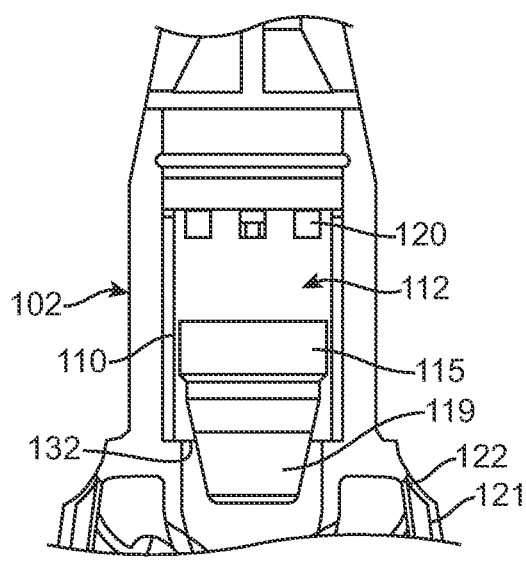
FIG. 15 is a view (to a further enlarged scale) of the actuator in the condition illustrated in FIG. 14e.

Referring now to FIG. 14e, the levers 121 have been moved through a further 14 degrees as compared to the position shown in FIG. 14d (and therefore 20 degrees from the initial position shown in FIG. 14a). During this further movement, the second actuator formations 125 continue to compress the walls 108 of the reservoir portion 104 causing liquid adhesive to be discharged therefrom. The liquid adhesive is able to flow through the annular gap now formed between the plug 112 and the mouth 106 and then along the flow channels 110 for ultimate discharge from the applicator tip assembly 103. During this further movement of the levers 121 (i.e. from the position shown in FIG. 14d to that in FIG. 14e) the plug 112 moves along the outlet portion 105 of the body 102 until it (the plug 112) abuts against the upstream end of the funnel region 130 of the applicator tip assembly 103. For the purposes of clarity this is shown in the much enlarged view of FIG. 15. It will be appreciated that liquid adhesive that has exited the downstream ends of the channels 110 is able to flow into the applicator tip assembly 3 via the catastellated formulations 120 provided on the plug 12.

The position of the levers 121 as depicted in FIG. 14e represents their maximum deflection towards each other. As the levers 121 are released from this position, adhesive is drawn back from the applicator tip 128 (as described previously) thereby preventing drips and improving application control.

Figure 16:
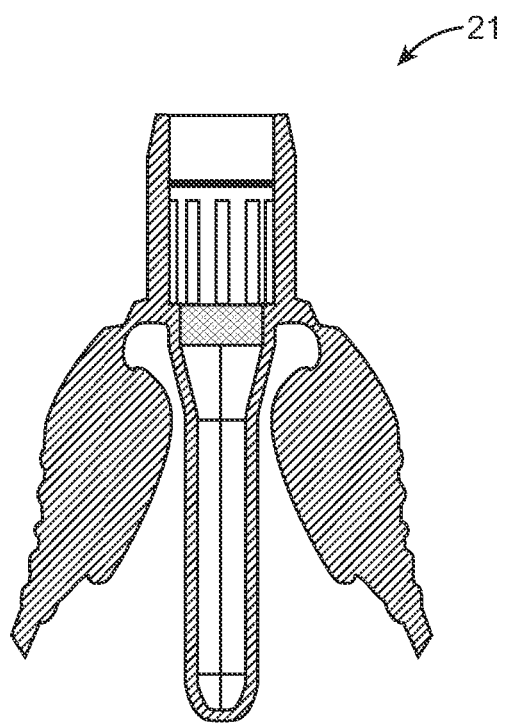
FIG. 16 is a cross-sectional view of the hollow body of a third embodiment of liquid applicator in accordance with the invention.
Figure 17:
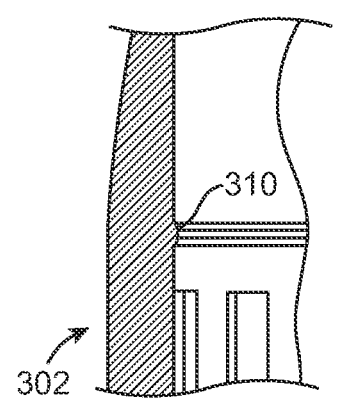
FIG. 17 is a detail to an enlarged scale of a region of the hollow body portion shown in FIG. 16.
Figure 18A:
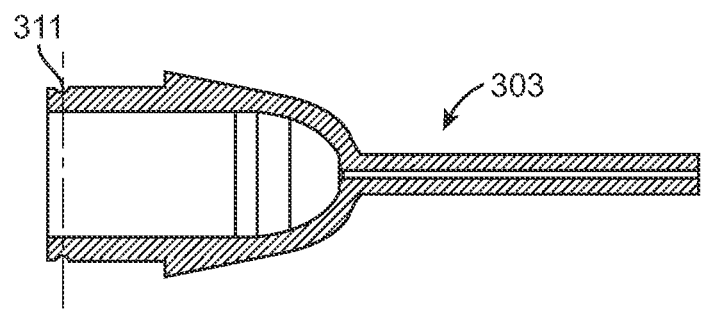
FIGS. 18a and 18b are respectively sectional and side views of an applicator tip assembly for use in conjunction with the body portion illustrated in FIG. 16.
Figure 18B:
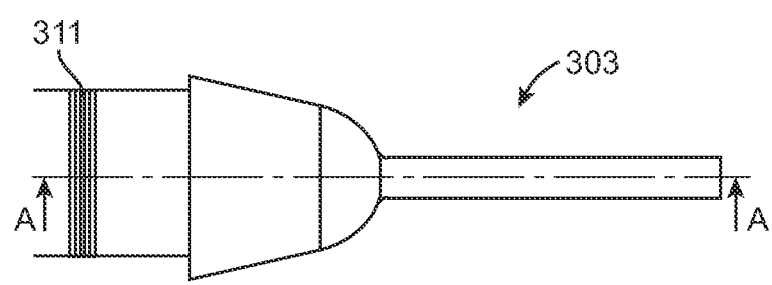

Reference is now made to the third embodiment of liquid applicator as shown in FIGS. 16-18 of the drawings for which (for convenience) parts corresponding with an equivalent part in the liquid applicator 1 are referenced by a numeral which is 300 greater than the corresponding reference numeral in FIGS. 1-9.

The hollow body portion 302 shown in FIG. 16 is very similar to the hollow body portion 102 shown in FIG. 11 but has an annular rib 310 (within the hollow body portion) instead of the annular groove 200 (see also the expanded view of FIG. 17).

Applicator assembly 303 (FIG. 18) incorporates a circumferential groove 311 in which the annular rib 310 is intended to locate whereby the body portion 302 and applicator assembly 303 are secured together.

Examples of cyanoacrylate adhesive compositions that may be incorporated in the applicator are given below.

The adhesive fluids that may be applied by the applicator of the present invention may be comprised of a wide variety of cyanoacrylate adhesive formulations. The reservoir may contain a stronger bonding and less flexible cyanoacrylate adhesive composition, such as n-butyl cyanoacrylate, or it may contain a more flexible tissue adhesive, such as an octyl or hexyl or decyl or other homologs of cyanoacrylate.

Preferably, the cyanoacrylate compositions used comprise cyanoacrylate prepolymer compositions that can be applied as a liquid/gel to the skin surface. Optionally, the cyanoacrylate prepolymers can include therapeutic agents such as analgesics, anti-inflammatory agents, antimicrobial agents, and the like.

Preferably, the polymerizable cyanoacrylate prepolymers comprise cyanoacrylate esters that, in monomeric form, are represented by the formula I:

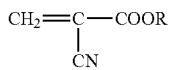

wherein
R is selected from the group consisting of:
alkyl of 1 to 10 carbon atoms,
alkenyl of 2 to 10 carbon atoms,
cycloalkyl groups of from 5 to 8 carbon atoms,
phenyl,
2-ethoxyethyl,
3-methoxybutyl,
and a substituent of the formula:

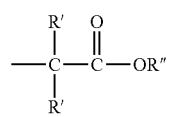

wherein
each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and phenyl substituted with 1 to 3 substituents selected from the group consisting of hydroxyl, chloro, bromo, nitro, alkyl of 1 to 4 carbon atoms, and alkoxy of from 1 to 4 carbon atoms.

More preferably, in the cyanoacrylate esters of formula I, R is an alkyl group of from 2 to 10 carbon atom including ethyl, n-propyl, iso-propyl, n-butyl, iso-butyl, sec-butyl, n-pentyl, iso-pentyl, n-hexyl, 2-ethylhexyl, n-heptyl, octyl, nonyl, and decyl. Mixtures of such compounds can also be employed as disclosed by Berger, et al., U.S. Pat. No. 5,998,472, which is incorporated herein by reference in its entirety.

It is to be understood that the term "polymerizable cyanoacrylate esters" refers to polymerizable formulations comprising cyanoacrylate monomers or polymerizable oligomers which, in their monomeric form, are preferably compounds represented by formula I as described above.

The polymerizable cyanoacrylate esters described herein rapidly polymerize in the presence of water vapour or tissue protein, and the n-butyl-cyanoacrylate bonds to mammalian skin tissue without causing histotoxicity or cytotoxicity.

Polymerizable cyanoacrylate esters are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

Optionally, the cyanoacrylate compositions applied by the present applicator can include a "biocompatible plasticizer". As used herein, the "biocompatible plasticizer" refers to any material which is soluble or dispersible in the cyanoacrylate composition, which increases the flexibility of the resulting polymeric film coating on the skin surface, and which, in the amounts employed, its compatible with the skin as measured by the lack of moderate to severe skin irritation. Suitable plasticizers are well known in the art and include those disclosed in U.S. Pat. Nos. 2,784,127 and 4,444,933 the disclosures of both of which are incorporated herein by reference in their entirety. Specific plasticizers include, by way of example only, acetyl tri-n-butyl citrate (preferably ~20 weight percent or less), acetyl trihexyl citrate (preferably ~20 weight percent or less) butyl benzyl phthalate, dibutyl phthalate, dioctylphthalate, n-butyryl tri-n-hexyl citrate, diethylene glycol dibenzoate (preferably ~20 weight percent or less) and the like. The particular biocompatible plasticizer employed is not critical and preferred plasticizers include dioctylphthalate and $C_2$-$C_4$-acyl tri-n-hexyl citrates.

Optionally as well, the cyanoacrylate composition applied by the present applicator can include an "antimicrobial agent". As used herein, the term "antimicrobial agent" refers to agents which destroy microbes (i.e. bacteria, fungi, yeasts and viruses) thereby preventing their development and their pathogenic action.

Preferred cyanoacrylate compositions useful in the practice of this invention are also disclosed by Greff, et al., U.S. Pat. No. 5,480,935, which application is incorporated herein by reference in its entirety. In a particularly preferred embodiment, the cyanoacrylate adhesive composition further comprises an antimicrobially effective amount of compatible antimicrobial agent. Such compositions preferably comprise from 0.1 to about 30 and preferably about 0.5 to 10 weight percent of the compatible antimicrobial agent either as a solution or as suspension based on the total weight of the composition. Compatible antimicrobial agents are those which are either soluble or suspendable in the cyanoacrylate composition, which do not cause premature polymerization of the cyanoacrylate composition, which do not prevent polymerization of the cyanoacrylate composition when applied to mammalian skin, and which are compatible with the intended use including biocompatibility with the patient's skin. Suitable such compositions of cyanoacrylate/povidone-iodine complexes, and U.S. Patent Application Ser. No. 60/498,913 filed on Aug. 29, 2003, which discloses compositions of cyanoacrylate esters and phenol. All three disclosures are incorporated herein by reference in their entirety.

The use of compatible antimicrobial agent in the compositions permits the agent to be released from the polymeric film thereby reducing microbial growth adjacent to the film.

Other medicaments suitable for use in conjunction with the cyanoacrylate compositions include corticoid steroids such as described by Greff, et al. in U.S. Pat. No. 5,962,010 which is incorporated herein by reference in its entirety and analgesic compounds such as lidocaine. The former reduces inflammation whereas the latter reduces pain. Combinations of a steroid with an analgesic are also covered.

It is to be understood that while the invention has been described in conjunction with the above embodiments, that the foregoing description is intended to illustrate and not limit the scope of the invention. Other aspects, advantages and modifications within the scope of the invention will be apparent to those skilled in the art to which the invention pertains.

What is claimed is:

1. A liquid applicator comprising:
   (a) a hollow body portion incorporating (i) a reservoir portion for containing a liquid to be applied by the applicator, and (ii) an outlet portion having first and second ends, the first end being connected to an outlet mouth of the reservoir, said outlet mouth having a mouth wall,
   (b) an applicator tip assembly provided on the second end of the outlet portion for discharge of liquid from the reservoir portion via said outlet portion,
   (c) a plug located in the mouth of the reservoir portion, said plug and mouth being configured so that the plug is moveable towards the applicator tip assembly from a first position at which it seals the reservoir portion to a second position at which fluid may follow out of the reservoir portion, and
   (d) a continuously curved actuator means for applying an actuating force to the mouth wall to effect movement of the plug towards the outlet portion, and for squeezing the walls of the reservoir portion to effect discharge of liquid from the reservoir portion via the outlet portion and the applicator device, wherein the actuator comprises a first actuator formation and a second actuator formation, with the first actuator formation being of more pronounced curvature than the second actuator formation.

2. An applicator as claimed in claim 1 wherein the inner surface of the outlet portion is formed with at least one channel that extends from the first end of the outlet portion towards the second end, the plug has a head that is a sliding fit on the inner surface of the outlet portion and a shank with a first portion that sealingly locates within the mouth of the reservoir portion, the arrangement being such that movement of the plug from the first to the second position allows fluid to flow from the reservoir portion said at least one channel to the applicator device.

3. An applicator as claimed in claim 2 wherein there is a step between said head and said first portion of the shank, the inner surface of the outlet portion of the body is provided with a shoulder that faces away from the reservoir portion and the step of the plug abuts against said shoulder when the plug is in its first position.

4. An applicator as claimed in claim 2 wherein a plurality of said channels are provided and extend parallel to each other.

5. An applicator as claimed in claim 4 wherein said channels are linear.

6. An applicator as claimed in claim 2 wherein the end of the head of the plug nearest the applicator tip assembly has a configuration to divert flow of liquid from along the flow channels inwardly towards the centre of the outlet portion for subsequent discharge via the applicator tip assembly.

7. An applicator as claimed in claim 6 wherein said configuration is provided by castellations extending around the periphery of said end of the head.

8. An applicator as claimed in claim 1 wherein said first portion of the shank has over a length thereof a cross-section which sealingly locates in a corresponding cross-section over a length of the mouth of the reservoir portion and movement of the plug to its second position causes said first portion of the shank to move out of the mouth of the reservoir portion.

9. An applicator as claimed in claim 8 wherein, at its end opposite the head, the plug has a second portion which is of lesser cross-section than said first portion.

10. An applicator as claimed in claim 1 wherein the first actuator formation for applying an actuating force to the mouth wall to effect movement of the plug towards the outlet portion, and the second actuator formation for squeezing the walls of the reservoir portion to effect discharge of liquid from the reservoir portion via the outlet portion and the applicator device.

11. An applicator as claimed in claim 10 wherein the mouth of the reservoir portion is formed with two opposed walls that converge towards each other in a direction going away from the applicator tip assembly, the applicator is provided with two said first actuator formations each of which is adapted to apply a actuating force to a respective one of said opposed converging walls to effect movement of the plug towards the second end of the outlet formation.

12. An applicator as claimed in claim 1 wherein the body is of high density polyethylene and the plug is of polypropylene.

13. An applicator as claimed in claim 1 containing a liquid.

14. An applicator as claimed in claim 13 wherein the liquid is a medical adhesive, sealant or coating.

15. An applicator as claimed in claim 13 or 14 wherein the liquid is a cyanoacrylate prepolymer.

16. The applicator of claim 1, further comprising a plurality of circumferentially spaced, axially extended grooves formed in the interior wall portion of the outlet portion and extend from the shoulder to the applicator tip assembly.

17. The applicator of claim 1 or 2, further comprising an annular grove or rib formed on the inner surface of the outlet portion in the hollow body.

* * * * *